(12) United States Patent (10) Patent No.: US 11,961,618 B2
Yuan et al. (45) Date of Patent: Apr. 16, 2024

(54) TASK INTERACTION NETWORK FOR PROSTATE CANCER DIAGNOSIS

(71) Applicant: City University of Hong Kong, Hong Kong (HK)

(72) Inventors: Yixuan Yuan, Hong Kong (HK); Meilu Zhu, Hong Kong (HK)

(73) Assignee: City University of Hong Kong, Hong Kong (HK)

( * ) Notice: Subject to any disclaimer, the term of this patent is extended or adjusted under 35 U.S.C. 154(b) by 407 days.

(21) Appl. No.: 17/528,207

(22) Filed: Nov. 17, 2021

(65) Prior Publication Data

US 2023/0154610 A1    May 18, 2023

(51) Int. Cl.
*G06K 9/00* (2022.01)
*G06T 7/00* (2017.01)
(Continued)

(52) U.S. Cl.
CPC ........... *G16H 50/20* (2018.01); *G06T 7/0014* (2013.01); *G06T 7/11* (2017.01);
(Continued)

(58) Field of Classification Search
CPC .............................. G06T 7/0012–0016; G06T 2207/10064–10136; G06T 2207/30004–30104; G06T 2207/30081; G06T 7/10–194; G06T 2207/20021; G06T 2207/20112–20168; G06T 2207/10088–10096;
(Continued)

(56) References Cited

U.S. PATENT DOCUMENTS 10,215,830 B2   2/2019   Kwak et al.
10,489,908 B2   11/2019  Kiraly et al.
(Continued)

OTHER PUBLICATIONS

Seetharaman, Bhattacharya, "Automated detection of aggressive and indolent prostate cancer on magnetic resonance", Medical Physics, Jun. 2021 (Year: 2021).*
(Continued)

*Primary Examiner* — Atiba O Fitzpatrick
(74) *Attorney, Agent, or Firm* — Idea Intellectual Limited; Margaret A. Burke; Sam T. Yip

(57) ABSTRACT

The present invention provides a task interaction network which can jointly perform, based on multi parametric-magnetic resonance imaging scan images, a segmentation task to locate prostate cancer areas and a classification task to access aggressiveness of lesions. The task interaction network comprises a backbone network, an auxiliary segmentation branch, a classification branch having a lesion awareness module, and a main segmentation branch having a category allocation module. The auxiliary segmentation branch is utilized to predict an initial lesion mask as location guidance information for the classification branch to perform the classification task. The lesion awareness module is configured to refine the initial lesion mask to make it more accurate. Moreover, weights used in classification branch can serve as the category prototypes for generating category guidance features via the category allocation module to assist the main segmentation branch to perform the segmentation task.

18 Claims, 6 Drawing Sheets

(51) Int. Cl.
*G06T 7/11* (2017.01)
*G16H 50/20* (2018.01)

(52) U.S. Cl.
CPC ............... *G06T 2207/10088* (2013.01); *G06T 2207/20081* (2013.01); *G06T 2207/30081* (2013.01); *G06T 2207/30096* (2013.01)

(58) Field of Classification Search
CPC ............. G06T 2207/10072–10136; G06T 2207/30032; G06T 2207/30096; G06T 2207/20081; G06T 2207/20084; G06V 2201/03–034; G06V 10/25–273; G06V 20/49; G06V 20/695; G06V 40/162; G06V 20/80; G06V 20/698; G06V 2201/032; G06V 10/87; G06V 30/19113; G06V 10/7753; G06V 10/70; G06V 10/82; G06V 10/774–7796; A61B 5/4381; A61B 5/7485; A61B 5/055; A61B 5/0263; A61B 6/02; A61B 6/025; A61B 6/027; A61B 6/03; A61B 6/032; A61B 6/037; G06K 9/6224; G06K 9/6256; G06K 9/6257; G06K 9/6259; G01R 33/5608; G01R 33/5635; G01R 33/48–58; A61K 49/06; A61N 5/1039; G01N 33/4833; G01N 15/10; G01N 2015/1006; G01N 33/505; G01N 33/5026; G01N 2015/1081; G06N 3/045; G06N 3/0455; G06N 3/0454; G06N 3/02–126; G06N 20/00–20; G06F 18/214–2155; G06F 7/023; G06F 40/16
See application file for complete search history.

(56) References Cited

U.S. PATENT DOCUMENTS

| | | | |
|---|---|---|---|
| 11,011,265 B2 | 5/2021 | Madabhushi et al. | |
| 2019/0183429 A1* | 6/2019 | Sung | A61B 5/7267 |
| 2019/0370965 A1* | 12/2019 | Lay | G06N 20/00 |
| 2020/0058126 A1* | 2/2020 | Wang | G06F 18/213 |
| 2020/0278408 A1* | 9/2020 | Sung | G06V 10/764 |
| 2021/0110534 A1* | 4/2021 | Yu | G06V 10/764 |
| 2021/0241027 A1* | 8/2021 | Hu | G06V 30/2504 |
| 2021/0383538 A1* | 12/2021 | Deasy | A61B 6/5211 |
| 2022/0208355 A1* | 6/2022 | Li | G06T 7/174 |
| 2023/0410301 A1* | 12/2023 | Rajagopal | G06T 7/12 |

OTHER PUBLICATIONS

R. Cao et al., "Joint Prostate Cancer Detection and Gleason Score Prediction in mp-MRI via FocalNet," in IEEE Transactions on Medical Imaging, vol. 38, No. 11, pp. 2496-2506, Nov. 2019, doi: 10.1109/TMI.2019.2901928. (Year: 2019).*

Zhenzhen Dai, Eric Carver, Chang Liu, Joon Lee, Aharon Feldman, Weiwei Zong, Milan, Pantelic, Mohamed Elshaikh, Ning Wen, "Segmentation of the Prostatic Gland and the Intraprostatic Lesions on Multiparametic MRI Using Mask-RCNN", Department of Radiation Oncology, Henry Ford Health System, Jun. 2, 2021 (Year: 2021).*

Y. Qian, Z. Zhang and B. Wang, "ProCDet: A New Method for Prostate Cancer Detection Based on MR Images," In IEEE Access, vol. 9, pp. 143495-143505, 2021, doi: 10.1109/ACCESS.2021.3114733. (Year: 2021).*

Le Vuong T T, Kim K, Song B, et al, "Joint categorical and ordinal learning for cancer grading in pathology images" in Medical Image Analysis, vol. 73, pp. 1-15, 2021: 102206.

De Vente C, Vos P, Hosseinzadeh M, et al, "Deep learning regression for prostate cancer detection and grading in bi-parametric MRI" in IEEE Transactions on Biomedical Engineering., vol. 68, No. 2, pp. 374-383, 2020.

Cao R, Bajgiran A M, Mirak S A, et al., "Joint prostate cancer detection and gleason score prediction in mp-MRI via FocalNet" in IEEE transactions on medical imaging., vol. 38, No. 11, pp. 2496-2506, 2019.

* cited by examiner

TASK INTERACTION NETWORK FOR PROSTATE CANCER DIAGNOSIS

COPYRIGHT NOTICE

A portion of the disclosure of this patent document contains material, which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE INVENTION

The present invention generally relates to machine learning prostate cancer diagnosis, more specifically, a task-interaction network (TI-Net) for prostate cancer diagnosis based on multi parametric-magnetic resonance imaging (mp-MRI) scan images.

BACKGROUND OF THE INVENTION

Prostate cancer is the most commonly diagnosed cancer and the second leading cause of cancer death among men. Early detection, diagnosis and treatment can improve the survival rate of patients. Multi-parametric MRI (mp-MRI) is one of the widely applied techniques for prostate cancer detection and risk assessment. However, interpreting mp-MRI sequences manually requires substantial expertise and labor from radiologists, and usually results in low sensitivity and specificity. Some existing technologies have been adopted to provide automatic prediction and diagnosis of prostate cancer by exploiting multiple networks to predict the aggressiveness and locations of prostate cancer lesion based on mp-MRI scans. However, these technologies consider these multiple tasks individually and ignore their complementary information, leading to limited performance and high overhead on run time.

SUMMARY OF THE INVENTION

The present invention provides a machine-learning task interaction network (TI-Net) which can assist radiologists to diagnose prostate cancer for patients based on multi parametric-magnetic resonance imaging (mp-MRI) scan images which include at least two types of MRI slides corresponding to two commonly used modalities respectively. In practice, it also can provide diagnosis reference for radiologists when the disease of patients is complicated. This invention can be applied into clinical scenarios to accelerate the time of disease diagnosis According to one aspect of the present invention, a task-interaction network is provided for jointly performing a segmentation task to locate prostate cancer areas and a classification task to assess aggressiveness of lesions based on a multi parametric-magnetic resonance imaging (mp-MRI) scan image in terms of a plurality of defined categories, the TI-Net comprising: a backbone network configured to extract an initial discriminative feature representation from an aligned and concatenated first and second type MRI slices of the mp-MRI scan image; an auxiliary segmentation branch configured to generate an initial probability map and predict an initial lesion mask based on the initial discriminative feature representation; a classification branch configured to determine a plurality of category prototypes corresponding to the plurality of defined categories respectively and predict a lesion aggressiveness based on the initial discriminative feature representation, the plurality of category prototypes and the initial lesion mask; and a main segmentation branch configured to predict a lesion location based on the initial discriminative feature representation, the plurality of category prototypes and the predicted lesion aggressiveness.

According to another aspect of the present invention, a method using the task-interaction network (TI-Net) is provided for jointly performing a segmentation task to locate prostate cancer areas and a classification task to assess aggressiveness of lesions based on a multi parametric-magnetic resonance imaging (mp-MRI) scan image in terms of a plurality of defined categories. The method comprising: extracting, by the backbone network, an initial discriminative feature representation from an aligned and concatenated first and second type MRI slices of the mp-MRI scan image; generating, by a probability mapping module in the auxiliary segmentation branch, an initial probability map based on the initial discriminative feature representation; performing, by an auxiliary segmentation module in the auxiliary segmentation branch, a softmax operation on the initial probability map to obtain an initial lesion mask; generating, by a lesion awareness module in the classification branch, a refined discriminative feature representation based on the initial lesion mask and the initial discriminative feature representation; determining, by a prototyping module in the classification branch, a plurality of category prototypes corresponding to the plurality of defined categories respectively; predicting, by a classification module in the classification branch, a lesion aggressiveness based on the refined discriminative feature representation and the plurality of category prototypes; generating, by a category allocation module in the main segmentation branch, a hybrid feature representation based on the initial discriminative feature representation, the plurality of category prototypes and the predicted lesion aggressiveness; and predicting, by a main segmentation module in the main segmentation branch, a lesion location based on the hybrid feature representation.

The auxiliary segmentation branch is utilized to predict an initial lesion mask as location guidance information for the classification branch to perform the classification task. The lesion awareness module is configured to refine the initial lesion mask to make it more accurate. Moreover, the weights used in classification branch can serve as the category prototypes for generating category guidance features via the category allocation module to assist the main segmentation branch to perform the segmentation task. For training the TI-Net, a consistency loss is optimized to enhance the mutual guidance among these two tasks and guarantee the consistency of the predictions.

Compared with existing technologies the present invention has the faster diagnosis speed as multiple tasks can be completed simultaneously via the TI-Net. The present invention is easier to be deployed in computer-aided design (CAD) system and does not require complicated hardware for implementation. Because the segmentation and classification tasks are highly related and provide complementary information for each other, the present invention can conduct deep task interaction and guarantee the prediction consistency of the two tasks while leveraging complementary information between the two modalities, thus improve diagnosis accuracy of prostate cancer detection which is very significant in practically clinical diagnosis.

BRIEF DESCRIPTION OF THE DRAWINGS

Embodiments of the invention are described in more detail hereinafter with reference to the drawings, in which.

DETAILED DESCRIPTION

In the following description, exemplary embodiments of the present invention are set forth as preferred examples. It will be apparent to those skilled in the art that modifications, including additions and/or substitutions may be made without departing from the scope and spirit of the invention. Specific details may be omitted so as not to obscure the invention; however, the disclosure is written to enable one skilled in the art to practice the teachings herein without undue experimentation.

Figure 1:
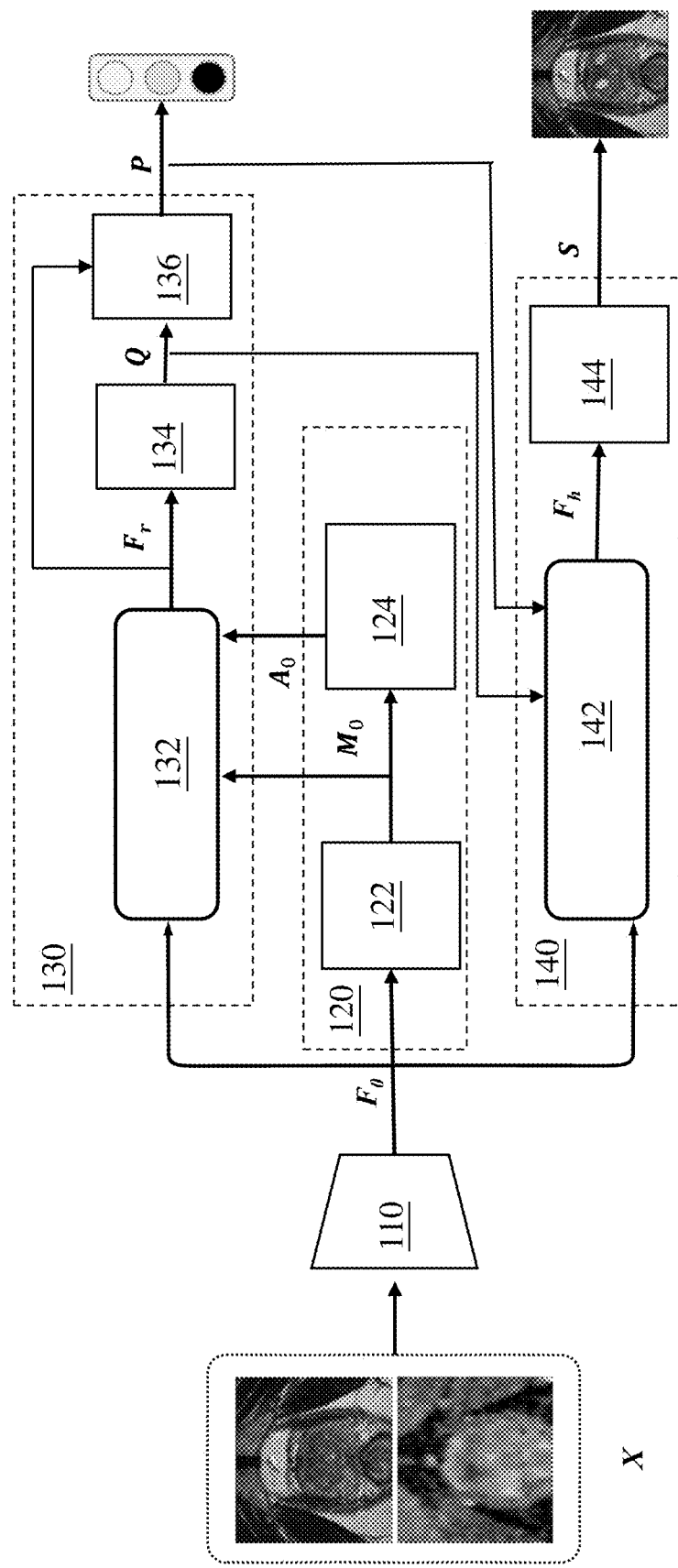
FIG. 1 depicts a block diagram of a task-interaction network (TI-Net) according to one embodiment of the present invention.

FIG. 1 shows a block diagram of a task-interaction network (TI-Net) 100 according to one embodiment of the present invention. As shown, the TI-Net 100 may comprise a backbone network 110, an auxiliary segmentation branch 120, a classification branch 130 and a main segmentation branch 140. The auxiliary segmentation branch 120 may include a probability mapping module 122 and an auxiliary segmentation module 124. The classification branch 130 may include a lesion awareness module 132, a prototyping module 134 and a classification module 136. The main segmentation branch 140 may include a category allocation module 142 and a main segmentation module 144.

The backbone network 110 may be a dilated convolution (atrous convolution) network such as DeeplabV3+ with Xception as encoder. The output stride of the backbone network may be set to 8. The main segmentation, auxiliary segmentation and classification branches share the first 20 blocks of convolution layers of the backbone network.

The probability mapping module 122 may consist of three convolutional layers. The first two layers are configured for providing non-linear mapping in feature extraction and the third layer is configured for batch normalization and dropout.

The TI-Net 100 may be trained and configured to jointly segment prostate cancer areas and assess aggressiveness of lesions from a multi parametric-magnetic resonance imaging (mp-MRI) scan image of a patient in terms of a plurality of defined categories. The mp-MRI scan image may include at least two types of MRI slides corresponding to two commonly used modalities respectively. The two commonly used modalities may provide correlated and complementary information to each other. In some embodiments, the two commonly used modalities may include T2-weight (T2w) and apparent diffusion coefficient (ADC).

Figure 2:
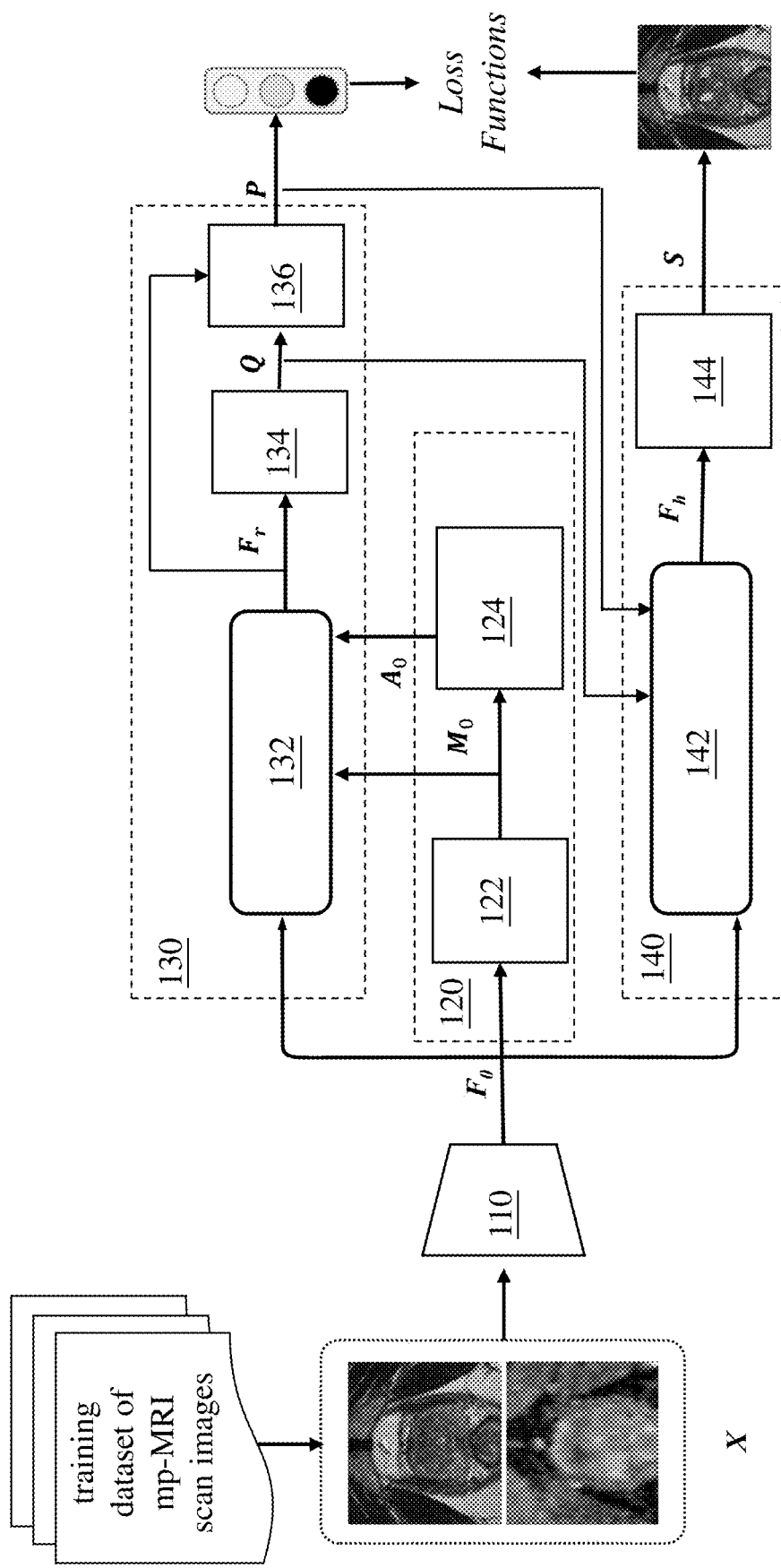
FIG. 2 depicts an arrangement for training a task-interaction network according to one embodiment of the present invention.

FIG. 2 shows an arrangement for training the TI-Net 100 using a training dataset of mp-MRI scan images categorized in terms of a plurality of categories of prostate cancer. The training dataset of mp-MRI scans are prepared such that each mp-MRI scan has at least a first type MRI slide and a second type MRI slide corresponding to two commonly used modalities respectively. By way of example, the first type MRI slice is a T2w MRI slice and the second type MRI slice is an ADC MRI slice. There are five categories of prostate cancer defined as:

Grade Group 1 (Gleason score <6): Only individual discrete well-formed glands;

Grade Group 2 (Gleason score 3+4=7): Predominantly well-formed glands with lesser component of poorly-formed/fused/cribriform glands;

Grade Group 3 (Gleason score 4+3=7): Predominantly poorly formed/fused/cribriform glands with lesser component of well-formed glands;

Grade Group 4 (Gleason score 4+4=8; 3+5=8; 5+3=8): (1) Only poorly-formed/fused/cribriform glands or (2) predominantly well-formed glands and lesser component lacking glands or (3) predominantly lacking glands and lesser component of well-formed glands; and Grade Group 5 (Gleason scores 9-10): Lacks gland formation (or with necrosis) with or without poorly formed/fused/cribriform glands.

The training dataset of mp-MRI scan images are preprocessed by registering the first type MRI slice with the second type MRI slice via non-rigid registration based on mutual information of the first and second type MRI slices; normalizing intensity of the first and second type MRI slices with zero mean and unit variance; center-cropping and resizing the first and second type MRI slices in an axial plane to reduce noisy from irrelevant information; and spatially aligning and concatenating the first and second type MRI slices. The aligned and concatenated first and second type MRI slices X are then fed into the TI-Net for training.

Referring to FIG. 2, the backbone network 110 may be configured and trained to extract an initial discriminative feature representation F from each pair of aligned and concatenated first and second type MRI slices X.

The auxiliary segmentation branch 120 may be configured and trained to generate an initial probability map $M_0$ and predict an initial lesion mask $A_0$ based on the initial discriminative feature representation $F_0$. In particular, the probability mapping module 122 may be configured and trained to generate the initial probability map $M_0$ based on the initial discriminative feature representation $F_0$. The auxiliary segmentation module 124 may be configured and trained to perform a softmax operation on the initial probability map $M_0$ to obtain the initial lesion mask $A_0$.

The classification branch 130 may be configured and trained to determine C category prototypes Q corresponding to the C categories respectively and predict a lesion aggressiveness P based on the initial discriminative feature representation $F_0$, the C category prototypes Q and the initial lesion mask $A_0$.

In particular, the lesion awareness module 132 may be configured and trained to generate a refined discriminative feature representation $F_r$ based on the initial lesion mask $A_0$ and the initial discriminative feature representation $F_0$; the prototyping module 134 may be configured and trained to determine the C category prototypes Q corresponding to the C defined categories respectively; and the classification module 136 may be configured and trained to predict the lesion aggressiveness P based on the refined discriminative feature representation $F_r$ and the C category prototypes Q.

Figure 3:
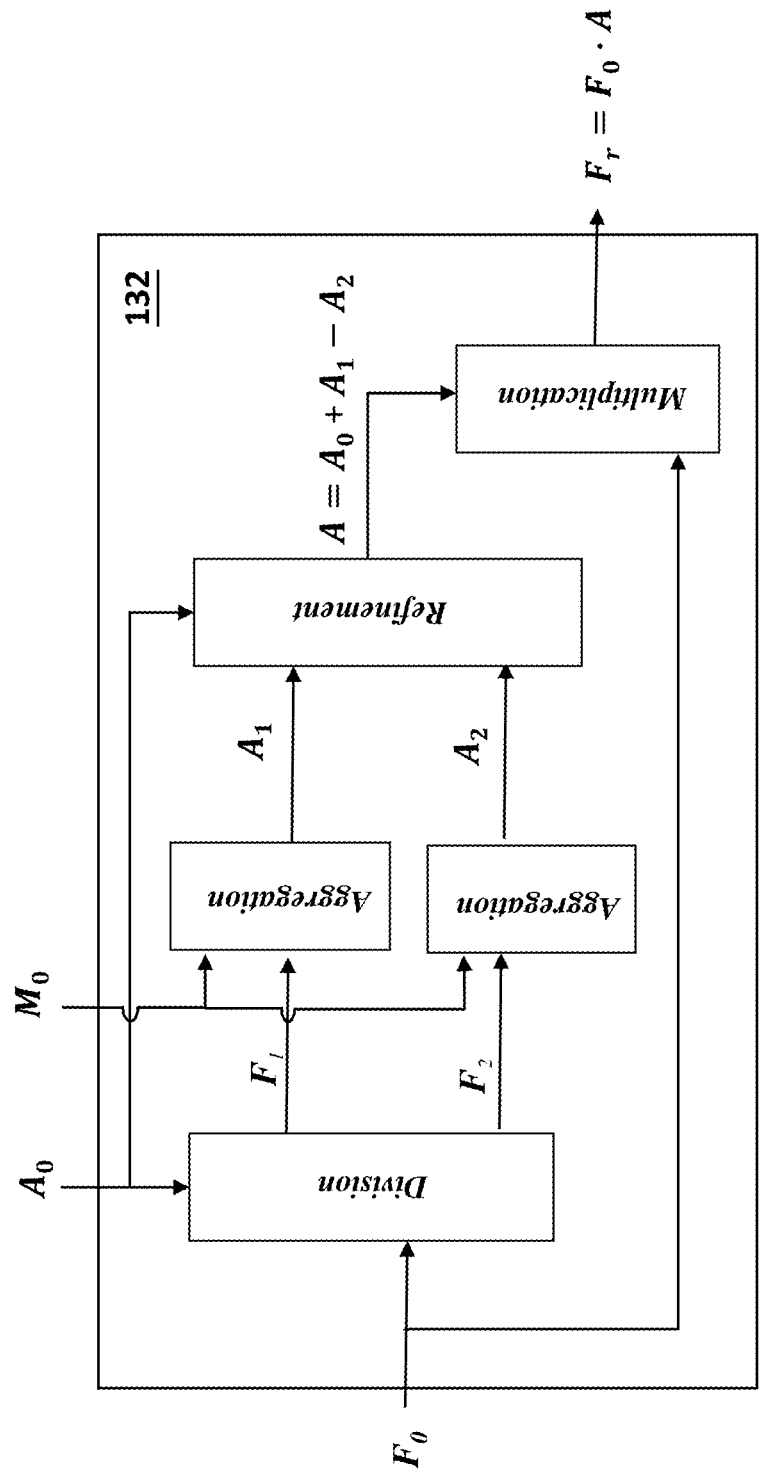
FIG. 3 depicts operation of a lesion awareness module according to one embodiment of the present invention.

Referring to FIG. 3, the lesion awareness module 132 may be configured and trained to divide the initial discriminative feature representation $F_0$ into a foreground feature representation $F_1$ and a background feature representation $F_2$ based on the initial lesion mask; obtain an aggregated foreground similarity map $A_1$ based on the foreground feature representation $F_1$; obtain an aggregated background similarity map $A_2$ based on the background feature representation $F_2$; refine the initial lesion mask $A_0$ by adding the aggregated foreground similarity map $A_1$ to and erasing the aggregated background similarity map $A_2$ from the initial lesion mask $A_0$ to obtain a refined lesion mask A (that is, $A=A_0+A_1-A_2$); and multiply the refined lesion mask A with the initial discriminative feature representation $F_0$ to obtain the refined discriminative feature representation $F_r$ (that is, $F_r=F_0 \cdot A$).

Preferably, the lesion awareness module 132 may be further configured and trained to index a K number of high-confidence foreground pixels in the foreground feature representation $F_1$ based on the initial probability map $M_0$; use each indexed foreground pixel to compute a cosine similarity with the background feature representation $F_2$ to obtain a K number of the foreground similarity maps; and fuse the K number of foreground similarity maps to obtain the aggregated foreground similarity map $A_1$.

Preferably, the lesion awareness module 132 may be further configured and trained to index a K number of high-confidence background pixels in the background feature representation $F_2$ based on the initial probability map $M_0$; use each indexed background pixel to compute a cosine similarity with the foreground feature representation $F_1$ to obtain a K number of background similarity maps; and fuse the K number of background similarity maps to obtain the aggregated background similarity map $A_2$.

Referring back to FIG. 2, the main segmentation branch 140 may be configured and trained to predict a lesion location S based on the initial discriminative feature representation $F_0$, the C category prototypes Q and the predicted lesion aggressiveness P.

In particular, the category allocation module 142 may be configured and trained to generate a hybrid feature representation $F_h$ based on the initial discriminative feature representation $F_0$, the C category prototypes Q and the predicted lesion aggressiveness P; and the main segmentation module 144 may be configured and trained to predict the lesion location S based on the hybrid feature representation $F_h$.

Figure 4:
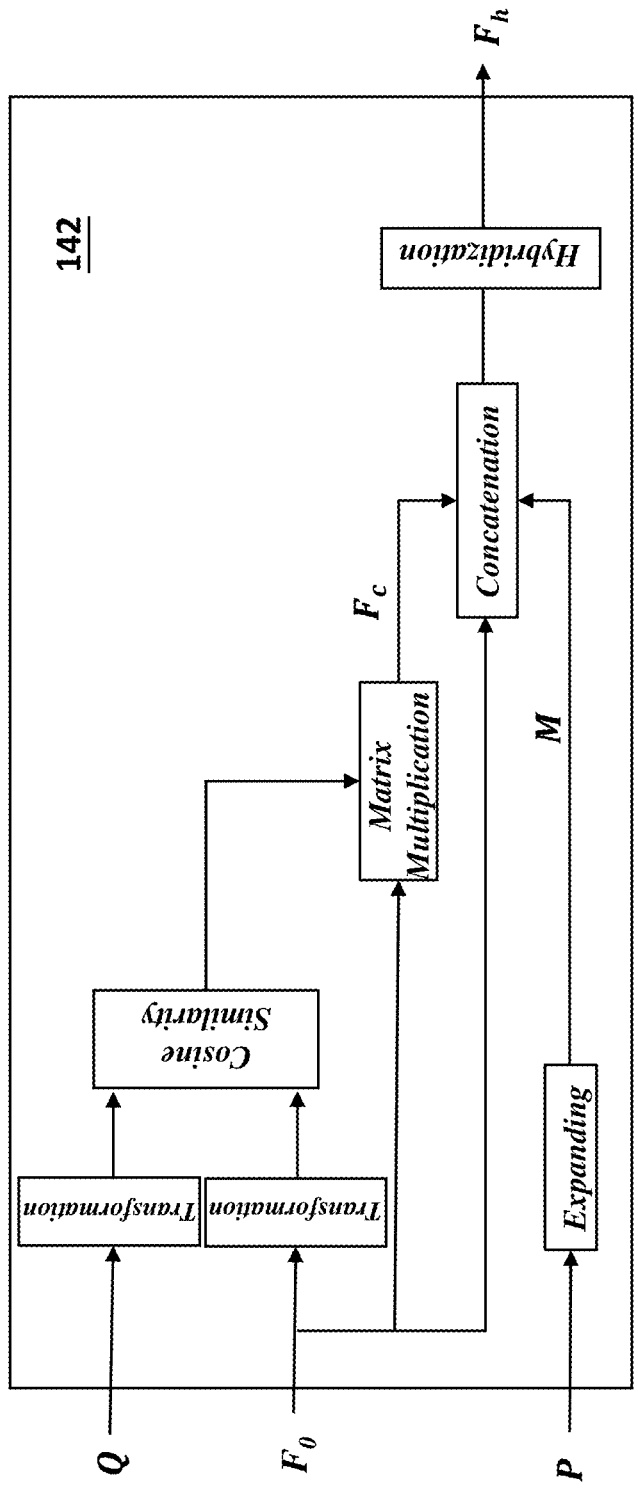
FIG. 4 depicts operation of a category allocation module according to one embodiment of the present invention.

Referring to FIG. 4, the category allocation module 142 may be configured and trained to expand the predicted lesion aggressiveness P to obtain a refined probability map M; transform the initial discriminative feature representation $F_0$ and the C category prototypes Q to have a same channel number; compute cosine similarity for each of the C transformed category prototypes Q with respect to the transformed discriminative feature representation $F_0$ to obtain C discriminative feature similarity maps; pass the C discriminative feature similarity maps through a softmax function with a temperature T to obtain C similarity values, where T is a hyper-parameter; compute a category-guided pixel-level feature representation for each pixel of the scan image by fusing the C category prototypes Q using the C similarity values as weights; integrate category-guided pixel-level feature representations for all pixels of the scan image into the initial discriminative feature representation $F_0$ to obtain a category-guided feature representation $F_c$; concatenate the initial discriminative feature representation $F_0$ and the category-guided feature representation $F_c$ with the refined probability map M to form a concatenated feature representation; and hybridize the concatenated feature representation to obtain the hybrid feature representation $F_h$.

The training of the classification branch and backbone network may be supervised with a multi-label loss function such that parameters in the backbone network and the classification branch can be updated through optimizing the multi-label loss function.

The multi-label loss function may be defined as:

$$L_1 = -\frac{1}{N}\Sigma_{i=1}^{N}\Sigma_{c=0}^{C} y_i^c \log \hat{y}_i^c + (1-y_i^c)\log(1-\hat{y}_i^c)$$

where $L_1$ is the multi-label loss, N is the number of training samples, C is the number of categories, $y_i^c$ and $\hat{y}_i^c$ are the prediction probability value and ground-truth value of i-th sample corresponding to c-th category respectively.

The training of the main segmentation branch and auxiliary segmentation branch may be supervised with a standard dice loss function such that parameters in the main segmentation branch and the auxiliary segmentation branch can be updated through optimizing the standard dice loss function.

The standard dice loss function may be defined as:

$$L_2 = \frac{2TP}{2TP+FP+FN},$$

where $L_2$ is the standard dice loss, TP is the number of true positives, FP is the number of false positives and FN is the numbers of false negatives.

The consistency between the lesion aggressiveness predictions P provided by the classification branch and the lesion location predictions S provided by the segmentation branch may be restrained with a mean squared error (MSE) loss function defined as:

$$L_3 = \frac{1}{2N}\Sigma_{i=1}^{N}\|P-S\|^2,$$

such that parameters in TI-Net may be updated jointly through optimizing the MSE loss function. In some embodiments, if P and S are not compatible, S may be first transformed into the same size with P by the average operation on the mask of each class before being evaluated with the MSE loss function.

By way of example, if the aggressiveness prediction shows Gleason score (GS) grading of a patient is normal (Gleason score <6) and there is no lesion area in output of segmentation branch, the patient should be health. If the aggressiveness prediction for a patient belongs to Grade Group 2-5 and the segmentation branch also illustrates that the corresponding lesion areas is same group, the diagnosis result obtained by the trained TI-Net for this patient will be confident. When the predictions of classification and segmentation branches are inconsistent, assistance of radiologists may be required to further analyze the patient's condition by refereeing to the predictions of two branches.

Figure 5:
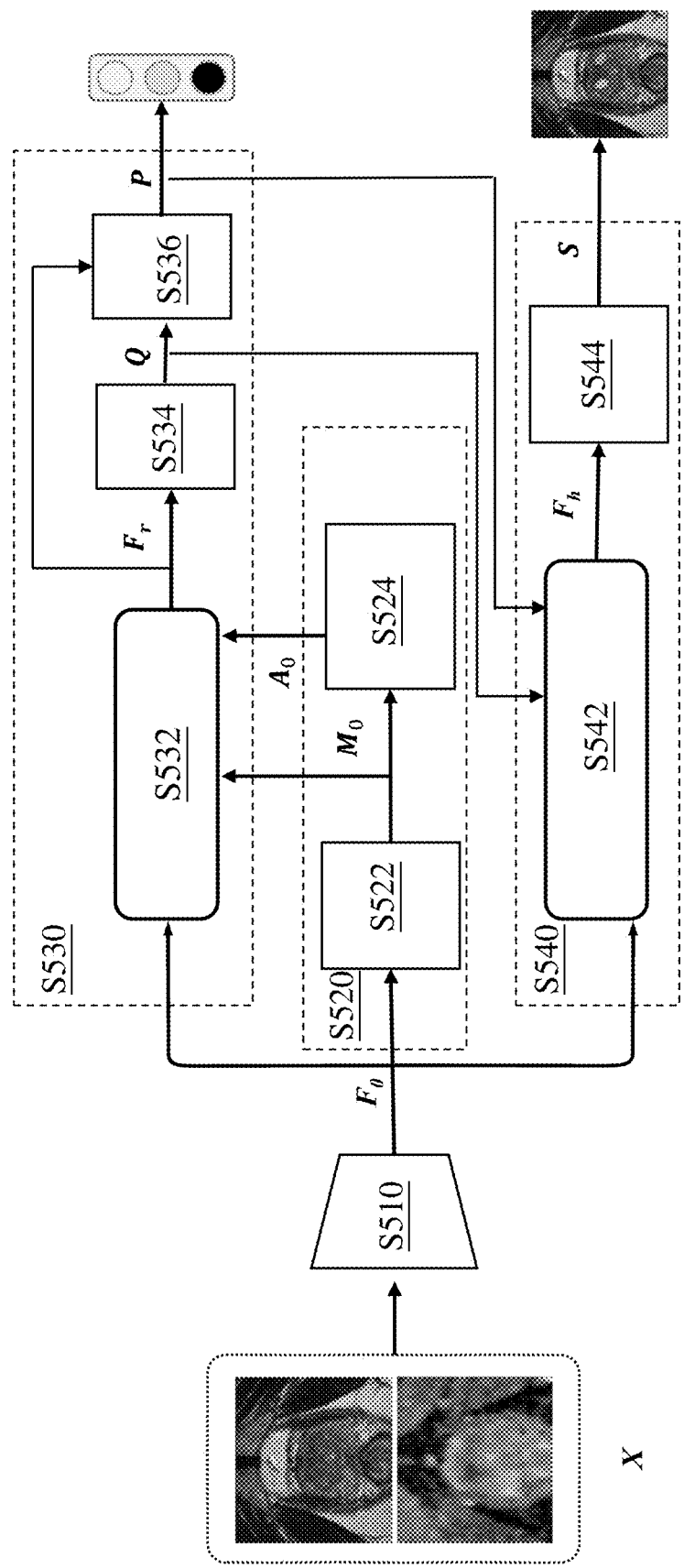
FIG. 5 depicts workflow of a method using a task-interaction network to provide prostate cancer diagnosis according to one embodiment of the present invention.

FIG. 5 shows workflow of a method using a TI-Net for jointly segmenting prostate cancer areas and assessing aggressiveness of lesions from a multi parametric-magnetic resonance imaging (mp-MRI) scan image in terms of a plurality of defined categories. As shown, the method may include a feature extraction stage S510, an auxiliary segmentation stage S520, a classification stage S530 and a main segmentation stage S540.

The feature extraction stage S510 include a step of extracting, by a backbone network of the TI-Net, an initial discriminative feature representation from an aligned and concatenated first and second type MRI slices of the mp-MRI scan image;

The auxiliary segmentation stage S520 includes:

Step S522: generating, by a probability mapping module in an auxiliary segmentation branch of the TI-Net, an initial probability map based on the initial discriminative feature representation; and Step S524: performing, by an auxiliary segmentation module in the auxiliary segmentation branch, a softmax operation on the initial probability map to obtain an initial lesion mask;

The classification stage S530 includes:

Step S532: generating, by a lesion awareness module in a classification branch of the TI-Net, a refined discriminative feature representation based on the initial lesion mask and the initial discriminative feature representation;

Step S534: determining, by a prototyping module in the classification branch, a plurality of category prototypes corresponding to the plurality of defined categories respectively; and Step S536: predicting, by a classification module in the classification branch, a lesion aggressiveness based on the refined discriminative feature representation;

The main segmentation stage S540 includes:

Step S542: generating, by a category allocation module in a main segmentation branch of the TI-Net, a hybrid feature representation based on the initial discriminative feature representation, the plurality of category prototypes and the predicted lesion aggressiveness; and Step S544: predicting, by a main segmentation module in the main segmentation branch, a lesion location based on the hybrid feature representation.

In some embodiments, to accelerate inference of network, a mixed-precision strategy may be introduced into the TI-Net. First, the input of prostate areas is scaled into half-precision floating point format (FP16). Therefore, the output of network is also half-precision, which is scaled back into single precision (FP32) to obtain final prediction. This strategy not only can reduce the demand on hardware memory, but also speed up the computation.

Figure 6:
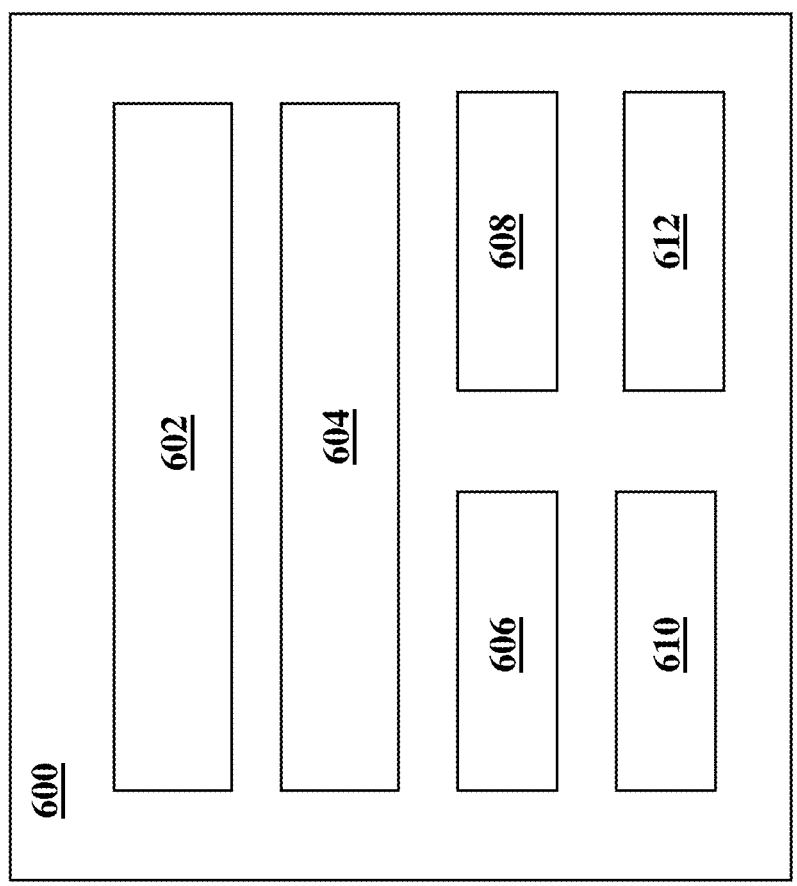
FIG. 6 is a block diagram of an exemplary hardware system for training and deploying a task-interaction network according to one embodiment of the present invention.

FIG. 6 is a block diagram of an exemplary system 600 for training and deploying a TI-Net according to one embodiment of the present invention. The system 600 can be any suitable computer-aided design (CAD) system. The system 600 may include at least one receiving module 602 configured for receiving or recording mp-MRI scans of a prostate of a patient.

The system 600 may further include a processor 604 which may be a CPU, an MCU, application specific integrated circuits (ASIC), field programmable gate arrays (FPGA) or any suitable programmable logic devices configured or programmed to be a processor for preprocessing the mp-MRI scans, training and deploying the TI-Net according to the teachings of the present disclosure.

The device 600 may further include a memory unit 606 which may include a volatile memory unit (such as RAM), a non-volatile unit (such as ROM, EPROM, EEPROM and flash memory) or both, or any type of media or devices suitable for storing instructions, codes, and/or data.

Preferably, the system 600 may further include one or more input devices 606 such as a keyboard, a mouse, a stylus, a microphone, a tactile input device (e.g., touch sensitive screen) and/or a video input device (e.g., camera). The system 600 may further include one or more output devices 610 such as one or more displays, speakers and/or disk drives. The displays may be a liquid crystal display, a light emitting display or any other suitable display that may or may not be touch sensitive.

The system 600 may also preferably include a communication module 612 for establishing one or more communication links (not shown) with one or more other computing devices such as a server, personal computers, terminals, wireless or handheld computing devices. The communication module 612 may be a modem, a Network Interface Card (NIC), an integrated network interface, a radio frequency transceiver, an optical port, an infrared port, a USB connection, or other interfaces. The communication links may be wired or wireless for communicating commands, instructions, information and/or data.

Preferably, the receiving module 602, the processing unit 604, the memory unit 606, and optionally the input devices 606, the output devices 610, the communication module 612 are connected with each other through a bus, a Peripheral Component Interconnect (PCI) such as PCI Express, a Universal Serial Bus (USB), and/or an optical bus structure. In one embodiment, some of these components may be connected through a network such as the Internet or a cloud computing network. A person skilled in the art would appreciate that the system 600 shown in FIG. 6 is merely exemplary, and that different systems 600 may have different configurations and still be applicable in the invention.

The foregoing description of the present invention has been provided for the purposes of illustration and description. It is not intended to be exhaustive or to limit the invention to the precise forms disclosed. Many modifications and variations will be apparent to the practitioner skilled in the art.

The apparatuses and the methods in accordance to embodiments disclosed herein may be implemented using computing devices, computer processors, or electronic circuitries and other programmable logic devices configured or programmed according to the teachings of the present disclosure. Computer instructions or software codes running in the computing devices, computer processors, or programmable logic devices can readily be prepared by practitioners skilled in the software or electronic art based on the teachings of the present disclosure.

All or portions of the methods in accordance to the embodiments may be executed in one or more computing devices including server computers, personal computers, laptop computers, mobile computing devices such as smartphones and tablet computers.

The embodiments were chosen and described in order to best explain the principles of the invention and its practical application, thereby enabling others skilled in the art to understand the invention for various embodiments and with various modifications that are suited to the particular use contemplated.

What is claimed is:

1. A task-interaction network (TI-Net) for jointly performing a segmentation task to locate prostate cancer areas and a classification task to assess aggressiveness of lesions based on a multi parametric-magnetic resonance imaging (mp-MRI) scan image in terms of a plurality of defined categories, the TI-Net comprising:

a backbone network configured to extract an initial discriminative feature representation from a pair of aligned and concatenated first and second type MRI slices of the mp-MRI scan image;

an auxiliary segmentation branch configured to generate an initial probability map and predict an initial lesion mask based on the initial discriminative feature representation;

a classification branch configured to determine a plurality of category prototypes corresponding to the plurality of defined categories respectively and predict a lesion aggressiveness based on the initial discriminative feature representation, the plurality of category prototypes and the initial lesion mask; and a main segmentation branch configured to predict a lesion location based on the initial discriminative feature representation, the plurality of category prototypes and the predicted lesion aggressiveness.

2. The task-interaction network according to claim 1, wherein the auxiliary segmentation branch includes:

a probability mapping module configured to generate the initial probability map based on the initial discriminative feature representation; and an auxiliary segmentation module configured to perform a softmax operation on the initial probability map to obtain the initial lesion mask.

3. The task-interaction network according to claim 1, wherein the classification branch includes:

a lesion awareness module configured to generate a refined discriminative feature representation based on the initial lesion mask and the initial discriminative feature representation;

a prototyping module configured to determine the plurality of category prototypes corresponding to the plurality of defined categories respectively; and a classification module configured to predict the lesion aggressiveness based on the refined discriminative feature representation and the plurality of category prototypes.

4. The task-interaction network according to claim 3, wherein the lesion awareness module is further configured to:

divide the initial discriminative feature representation into a foreground feature representation and a background feature representation based on the initial lesion mask;

obtain an aggregated foreground similarity map based on the foreground feature representation;

obtain an aggregated background similarity map based on the background feature representation;

refine the initial lesion mask by adding the aggregated foreground similarity map to and erasing the aggregated background similarity map from the initial lesion mask to obtain a refined lesion mask; and multiply the refined lesion mask with the initial discriminative feature representation to obtain the refined discriminative feature representation.

5. The task-interaction network according to claim 4, wherein the lesion awareness module is further configured to:

index a plurality of high-confidence foreground pixels in the foreground feature representation based on the initial probability map;

use each indexed foreground pixel to compute a cosine similarity with the background feature representation to obtain a plurality of foreground similarity maps; and fuse the plurality of foreground similarity maps to obtain the aggregated foreground similarity map.

6. The task-interaction network according to claim 4, wherein the lesion awareness module is further configured to:

index a plurality of high-confidence background pixels in the background feature representation based on the initial probability map;

use each indexed background pixel to compute a cosine similarity with the foreground feature representation to obtain a plurality of background similarity maps; and fuse the plurality of background similarity maps to obtain the aggregated background similarity map.

7. The task-interaction network according to claim 1, wherein the main segmentation branch includes:

a category allocation module configured to generate a hybrid feature representation based on the initial discriminative feature representation, the plurality of category prototypes and the predicted lesion aggressiveness; and a main segmentation module configured to predict the lesion location based on the hybrid feature representation.

8. The task-interaction network according to claim 7, wherein the category allocation module is further configured to:

expand the predicted lesion aggressiveness to obtain a refined probability map;

transform the initial discriminative feature representation and the plurality of category prototypes to have a same channel number;

compute cosine similarity for each of the plurality of transformed category prototypes with respect to the transformed discriminative feature representation to obtain a plurality of discriminative feature similarity maps;

pass the plurality of discriminative feature similarity maps through a softmax function with a temperature T to obtain a plurality of similarity values, where T is a hyper-parameter;

compute a category-guided pixel-level feature representation for each pixel of the scan image by fusing the plurality of category prototypes using the plurality of similarity values as weights;

integrate category-guided pixel-level feature representations for all pixels of the scan image to obtain a category-guided feature representation;

concatenate the initial discriminative feature representation and the category-guided feature representation with the refined probability map to form a concatenated feature representation; and hybridize the concatenated feature representation to form the hybrid feature representation.

9. A method for training a task-interaction network (TI-Net) to jointly perform a segmentation task to locate prostate cancer areas and a classification task to assess aggressiveness of lesions based on a multi parametric-magnetic resonance imaging (mp-MRI) scan image in terms of a plurality of defined categories, the method comprising:

preparing a training dataset of mp-MRI images, each mp-MRI image having a labelled category and including a first type MRI slice and a second type MRI slice;

for each mp-MRI image:

registering the first type MRI slice with the second type MRI slice via non-rigid registration based on mutual information of the first and second type MRI slices;

normalizing intensity of the registered first and second type MRI slices with zero mean and unit variance;

center-cropping and resizing the normalized first and second type MRI slices in an axial plane to reduce noisy from irrelevant information;

spatially aligning and concatenating the cropped and resized first and second type MRI slices;

feeding the aligned and concatenated first and second type MRI slices to the TI-Net;

training a backbone network in the TI-Net to extract an initial discriminative feature representation from the aligned and concatenated first and second type MRI slices;

training an auxiliary segmentation branch in the TI-Net to generate an initial probability map and predict an initial lesion mask based on the initial discriminative feature representation;

training a classification branch in the TI-Net to determine a plurality of category prototypes corresponding to the plurality of defined categories respectively and predict a lesion aggressiveness based on the initial discriminative feature representation, the plurality of category prototypes and the initial lesion mask; and training a main segmentation branch in the TI-Net to predict a lesion location based on the initial discriminative feature representation, the plurality of category prototypes and the predicted lesion aggressiveness.

10. The method according to claim 9, wherein the first type MRI slice is a T2-weighted MRI slice and the second type MRI slice is an apparent diffusion coefficient MRI slice.

11. The method according to claim 9, further comprising updating parameters in the backbone network and the classification branch under supervision with a multi-label loss function defined as:

$$L_1 = -\frac{1}{N}\sum_{i=1}^{N}\sum_{c=0}^{C} y_i^c \log \hat{y}_i^c + (1 - y_i^c)\log(1 - \hat{y}_i^c)$$

where $L_1$ is the multi-label loss, N is the number of training samples, the plurality of is the number of classes, $y_i^c$ and $\hat{y}_i^c$ are the prediction probability value and ground-truth value of i-th sample corresponding to c-th class respectively.

12. The method according to claim 9, further comprising updating parameters in the main segmentation branch and auxiliary segmentation branch under supervision with a standard dice loss function defined by:

$$L_2 = \frac{2TP}{2TP + FP + FN},$$

where $L_2$ is the standard dice loss, TP is the number of true positives, FP is the number of false positives and FN is the numbers of false negatives.

13. The method according to claim 9, further comprising jointly updating parameters in the backbone network, the classification branch, the main segmentation branch and the auxiliary segmentation branch by restraining consistency between the predicted lesion aggressiveness and the predicted lesion location with a mean squared error (MSE) loss function defined by:

$$L_3 = \frac{1}{2N}\Sigma_{i=1}^{N}\|P - S\|^2.$$

14. A method using a task-interaction network (TI-Net) for jointly performing a segmentation task to locate prostate cancer areas and a classification task to assess aggressiveness of lesions based on a multi parametric-magnetic resonance imaging (mp-MRI) scan image in terms of a plurality of defined categories, the TI-Net including a backbone network, an auxiliary segmentation branch, a classification branch and a main segmentation branch, the method comprising:

extracting, by the backbone network, an initial discriminative feature representation from an aligned and concatenated first and second type MRI slices of the mp-MRI scan image;

generating, by a probability mapping module in the auxiliary segmentation branch, an initial probability map based on the initial discriminative feature representation;

performing, by an auxiliary segmentation module in the auxiliary segmentation branch, a softmax operation on the initial probability map to obtain an initial lesion mask;

generating, by a lesion awareness module in the classification branch, a refined discriminative feature representation based on the initial lesion mask and the initial discriminative feature representation;

determining, by a prototyping module in the classification branch, a plurality of category prototypes corresponding to the plurality of defined categories respectively;

predicting, by a classification module in the classification branch, a lesion aggressiveness based on the refined discriminative feature representation and the plurality of category prototypes;

generating, by a category allocation module in the main segmentation branch, a hybrid feature representation based on the initial discriminative feature representation, the plurality of category prototypes and the predicted lesion aggressiveness; and predicting, by a main segmentation module in the main segmentation branch, a lesion location based on the hybrid feature representation.

15. The method according to claim 14, wherein the refined discriminative feature representation is obtained by:

dividing the initial discriminative feature representation into a foreground feature representation and a background feature representation based on the initial lesion mask;

obtaining an aggregated foreground similarity map based on the foreground feature representation;

obtaining an aggregated background similarity map based on the background feature representation;

refining the initial lesion mask by adding the aggregated foreground similarity map to and erasing the aggregated background similarity map from the initial lesion mask to obtain a refined lesion mask; and multiplying the refined lesion mask with the initial discriminative feature representation to obtain the refined discriminative feature representation.

16. The method according to claim 15, wherein the aggregated foreground similarity map is obtained by:

indexing a plurality of high-confidence foreground pixels in the foreground feature representation based on the initial probability map;

using each indexed foreground pixel to compute a cosine similarity with the background feature representation to obtain a plurality of foreground similarity maps; and fusing the plurality of foreground similarity maps to obtain the aggregated foreground similarity map.

17. The method according to claim 15, wherein the aggregated background similarity map is obtained by:
- indexing a plurality of high-confidence background pixels in the background feature representation based on the initial probability map;
- using each indexed background pixel to compute a cosine similarity with the foreground feature representation to obtain a plurality of background similarity maps; and
- fusing the plurality of background similarity maps to obtain the aggregated background similarity map.

18. The method according to claim 15, wherein the hybrid feature representation is generated by:
- expanding the predicted lesion aggressiveness to obtain a refined probability map;
- transforming the initial discriminative feature representation and the plurality of category prototypes to have a same channel number;
- computing cosine similarity for each of the plurality of transformed category prototypes with respect to the transformed discriminative feature representation to obtain a plurality of discriminative feature similarity maps;
- passing the plurality of discriminative feature similarity maps through a softmax function with a temperature T to obtain a plurality of similarity values, where T is a hyper-parameter;
- computing a category-guided pixel-level feature representation for each pixel of the scan image by fusing the plurality of category prototypes using the plurality of similarity values as weights;
- integrating category-guided pixel-level feature representations for all pixels of the scan image to obtain a category-guided feature representation;
- concatenating the initial discriminative feature representation and the category-guided feature representation with the refined probability map to form a concatenated feature representation; and
- hybridizing the concatenated feature representation to form the hybrid feature representation.

* * * * *